(12) United States Patent
Flora

(10) Patent No.: US 6,971,385 B1
(45) Date of Patent: Dec. 6, 2005

(54) APPARATUS AND METHOD FOR RESPIRATORY DRUG DELIVERY

(76) Inventor: Maurino Flora, 4589 Encanto Way, San Jose, CA (US) 95135

(*) Notice: Subject to any disclaimer, the term of this patent is extended or adjusted under 35 U.S.C. 154(b) by 17 days.

(21) Appl. No.: 10/435,425

(22) Filed: May 9, 2003

(51) Int. Cl.[7] .................................... A61M 15/00
(52) U.S. Cl. ..................... 128/203.21; 128/205.21
(58) Field of Search ................... 128/200.22, 203.21, 128/205.21; 239/302–304, 308–311, 271, 239/272; 222/4, 5, 82, 83, 83.5, 85, 86, 129

(56) References Cited

U.S. PATENT DOCUMENTS

| | | | | |
|---|---|---|---|---|
| 2,641,253 A | * | 6/1953 | Engelder | 128/203.21 |
| 2,944,547 A | * | 7/1960 | Kish et al. | 128/203.21 |
| 3,012,694 A | * | 12/1961 | Johnston | 222/5 |
| 3,155,573 A | * | 11/1964 | Fowler | 424/40 |
| 3,425,414 A | * | 2/1969 | Roche | 128/203.21 |
| 3,470,874 A | * | 10/1969 | Accetta | 128/200.14 |
| 3,603,483 A | * | 9/1971 | Morane et al. | 222/82 |
| 3,730,392 A | * | 5/1973 | Marand | 222/82 |
| 3,809,289 A | * | 5/1974 | Komendowski | 222/83 |
| 3,848,773 A | * | 11/1974 | Adler et al. | 222/1 |
| 4,385,714 A | * | 5/1983 | Szabo et al. | 222/80 |
| 4,883,049 A | * | 11/1989 | McDonald | 128/202.22 |
| 4,887,591 A | * | 12/1989 | Okumura | 128/205.21 |
| 4,934,358 A | * | 6/1990 | Nilsson et al. | 128/200.23 |
| 5,002,048 A | * | 3/1991 | Makiej, Jr. | 128/200.23 |
| 5,007,419 A | * | 4/1991 | Weinstein et al. | 128/200.23 |
| 5,169,029 A | * | 12/1992 | Behar et al. | 222/1 |
| 5,273,190 A | * | 12/1993 | Lund | 222/83 |
| 5,287,850 A | * | 2/1994 | Haber et al. | 128/203.21 |
| 5,293,865 A | * | 3/1994 | Altner et al. | 128/203.12 |
| 5,437,267 A | * | 8/1995 | Weinstein et al. | 128/200.23 |
| 5,488,946 A | * | 2/1996 | Calhoun et al. | 128/205.21 |
| 5,535,736 A | * | 7/1996 | Jzaw | 128/202.26 |
| 5,544,646 A | * | 8/1996 | Lloyd et al. | 128/200.14 |
| 5,823,181 A | * | 10/1998 | Shih | 128/202.26 |
| 5,875,776 A | * | 3/1999 | Vaghefi | 128/203.15 |
| 6,070,573 A | * | 6/2000 | Howe et al. | 128/200.14 |
| 6,149,873 A | * | 11/2000 | Potter et al. | 422/123 |
| 6,347,725 B1 | * | 2/2002 | Yoakim et al. | 222/82 |
| 6,488,894 B1 | * | 12/2002 | Miethe et al. | 422/100 |
| 6,543,448 B1 | | 4/2003 | Smith et al. | |
| 6,571,790 B1 | * | 6/2003 | Weinstein | 128/200.19 |

FOREIGN PATENT DOCUMENTS

EP    0 469 814 A1 *  2/1992

* cited by examiner

Primary Examiner—Aaron J. Lewis
(74) Attorney, Agent, or Firm—Fernandez & Associates LLP

(57) ABSTRACT

Apparatus and method for respiratory drug delivery using cartridge containing drug and propellant. User inserts cartridge into body of apparatus and activates piercing trigger to pierce drug compartment and propellant compartment, resulting in mixing and de-agglomeration of drug for respiratory delivery.

10 Claims, 25 Drawing Sheets

```
701 Place cartridge
  ↓
702 Pierce drug compartment
  ↓
703 Pierce propellant compartment
  ↓
704 Aerosolize drug
```

Figure 7

APPARATUS AND METHOD FOR RESPIRATORY DRUG DELIVERY

BACKGROUND INFORMATION

1. Field of Invention

Invention relates to drug delivery systems, and in particular to respiratory drug delivery systems.

2. Description of Related Art

Current respiratory drug delivery systems are either bulky, expensive to produce, or require user to pump a device to pressurize air. Other shortcomings include: inconsistency of dose and the requirement of forceful inspiratory flow rate; time dependent dose variability due either to device reliability (wear and tear) or progressive decrease in drug canister pressure; and Non-specific drug delivery and the inability to distinguish between drug delivery for child or adult.

Accordingly, there is a need for a low cost, compact, reliable, repeatable, easy to use, drug delivery system distinguishing between doses for children or adults.

SUMMARY OF INVENTION

Apparatus and method for respiratory drug delivery using drug cartridge having drug and propellant compartments. Activation of piercing trigger causes piercing of drug compartment and propellant compartment, resulting in mixing and de-agglomeration of drug and subsequent aerosolization of drug for respiratory delivery.

BRIEF DESCRIPTION OF DRAWINGS

FIG. 1-*a* is a diagram illustrating a respiratory drug delivery system in open position, according to one embodiment of the present invention.

FIG. 1-*b* is a diagram illustrating a respiratory drug delivery system in closed position, according to one embodiment of the present invention.

FIG. 2-*a* is a diagram illustrating tapered mouthpiece, according to one embodiments of the present invention.

FIG. 2-*b* is a diagram illustrating bent mouthpiece, according to one embodiments of the present invention.

FIG. 2-*c* is a diagram illustrating grooved mouthpiece, according to one embodiments of the present invention.

FIG. 2-*d* is a diagram illustrating a respiratory drug delivery system with optional spacer, according to one embodiment of the present invention.

FIGS. 3-*a*1 and 3-*a*2 are diagrams illustrating cross-section of a single-tubing piercing mechanism, according to one embodiment of the present invention.

FIGS. 3-*b*1 and 3-*b*2 are diagrams illustrating a cross-section of a multi-tubing piercing mechanism, according to one embodiment of the present invention.

FIG. 3-*c* is a diagram illustrating cross-section of bumped piercing mechanism, according to one embodiment of the present invention.

FIG. 3-*d* is a diagram illustrating necked cross-section of pierce tubing, according to one embodiment of the present invention.

FIG. 3-*e* is a diagram illustrating detail of piercing head, according to one embodiment of the present invention.

FIG. 3-*f* is a diagram showing simulation of propellant and drug flow through pierce tubing, according to one embodiment of the present invention.

FIG. 3-*g* is a diagram illustrating a tip of the pierce head and corresponding membrane puncture, according to one embodiment of the present invention.

FIG. 3-*h* is a diagram illustrating a disposable cartridge with spring-loaded plunger mechanism, according to one embodiment of the present invention.

FIG. 3-*i* is a diagram illustrating a disposable cartridge with compressed-elastomer piercing mechanism, according to one embodiment of the present invention.

FIG. 3-*j* is a diagram illustrating a reusable cartridge with spring-loaded plunging mechanism, according to one embodiment of the present invention.

FIG. 3-*k* is a diagram illustrating a reusable cartridge with spring-loaded piercing mechanism, according to one embodiment of the present invention.

FIG. 4-*a* is a diagram illustrating a drug cartridge with one drug compartment and one gas compartment, according to one embodiment of the present invention.

FIG. 4-*b* is a diagram illustrating a divided drug or propellant compartment, according to one embodiment of the present invention.

FIG. 4-*c* is a diagram illustrating a drug cartridge with a drug reservoir, according to one embodiment of the present invention.

FIG. 4-*d* is a diagram illustrating a drug cartridge with two drug compartments and one gas compartment.

FIG. 4-*e* is a diagram illustrating a multi-dose rotary cartridge configuration, according to one embodiment of the present invention.

FIG. 4-*f* is a diagram illustrating a roll-up linear cartridge configuration, according to one embodiment of the present invention.

FIG. 4-*g* is a diagram illustrating a cartridge configuration with flow resistance flaps, according to one embodiment of the present invention.

FIG. 5-*a* is a diagram illustrating a micro-version of the respiratory drug delivery system, according to one embodiment of the present invention.

FIG. 5-*b* is a diagram illustrating a micro-version of the respiratory drug delivery system in closed position, according to one embodiment of the present invention.

FIG. 6 is a diagram illustrating optional locators on drug cartridge, according to one embodiment of the present invention.

FIG. 7 is a flow chart illustrating a method for respiratory drug delivery, according to one embodiment of the present invention.

DETAILED DESCRIPTION

Following glossary will serve as a guide to the terms used herein:

Drug: Any drug or particles (such as Albuterol, Insulin, Budesonide, aromatherapy powder) or other substance for respiratory delivery.

Propellant: Air, stable gas, a combination of gases and/or materials, or other substance for aerosolizing a drug. Propellant may reside in a compartment at a specific volume or pressure, or reside in a compartment unpressurized.

Aerosolize: Disperse as an aerosol, i.e. as a suspension of small particles (such as drug particles) in air, stable gas, a combination of gases and/or materials, or other substance.

Chaser: Compressed air, stable gas, a combination of gases or materials, or other substance for providing improved drug deposition via secondary push or flow, optionally distinct from propellant.

Membrane: Material for separating a first drug or propellant or chaser from a second drug or propellant or chaser, such as a single-layer or multi-layer plastic, or metallic material such as aluminum or other metallic foil, or Polyethyleneterephthalate (PET), or High Density Polyethylene (HDPE), or other material for said separating.

Figure 1A:
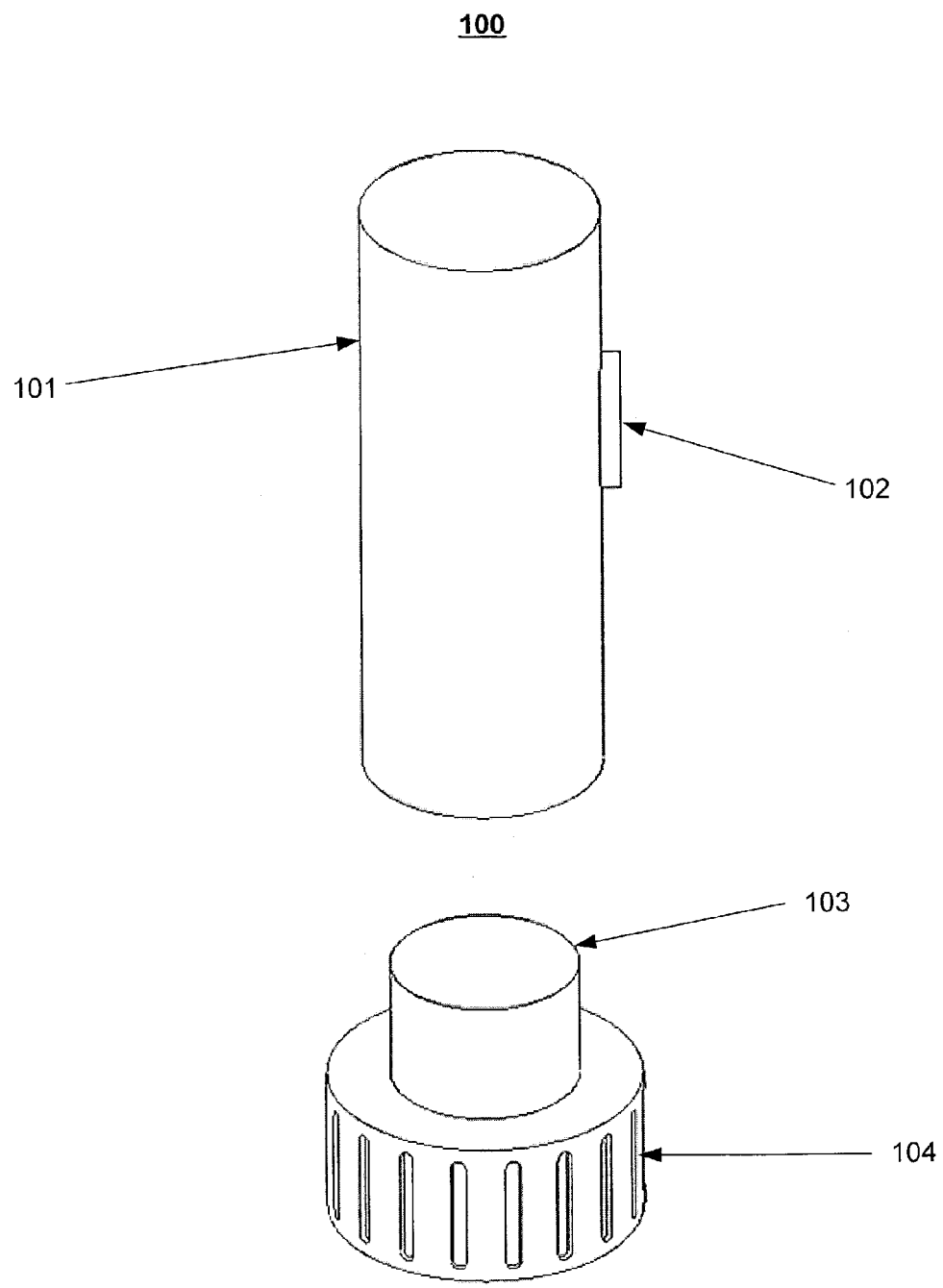
Figure 1B:
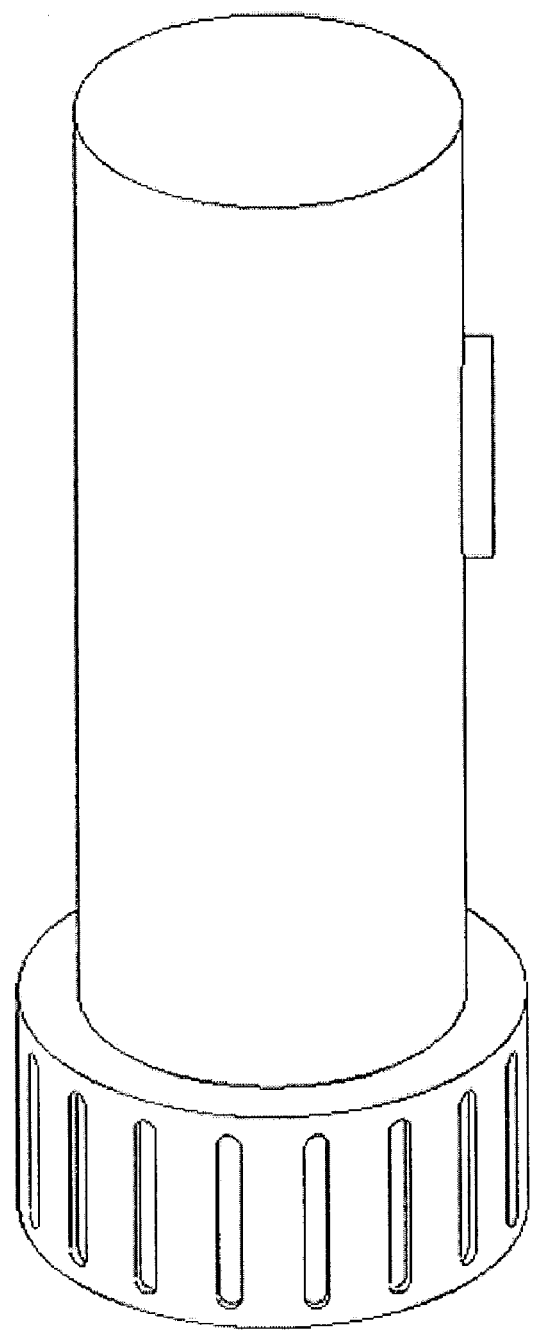
Figures 2A, 2B, 2C:
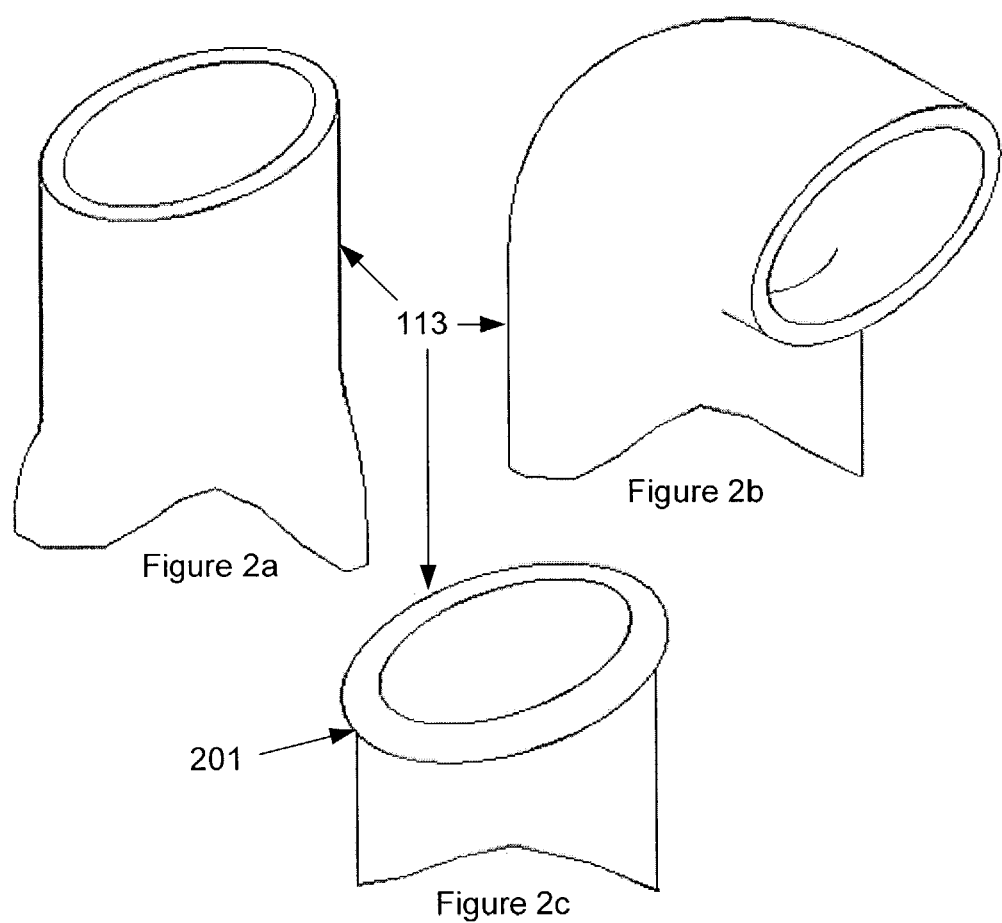
Figure 2D:
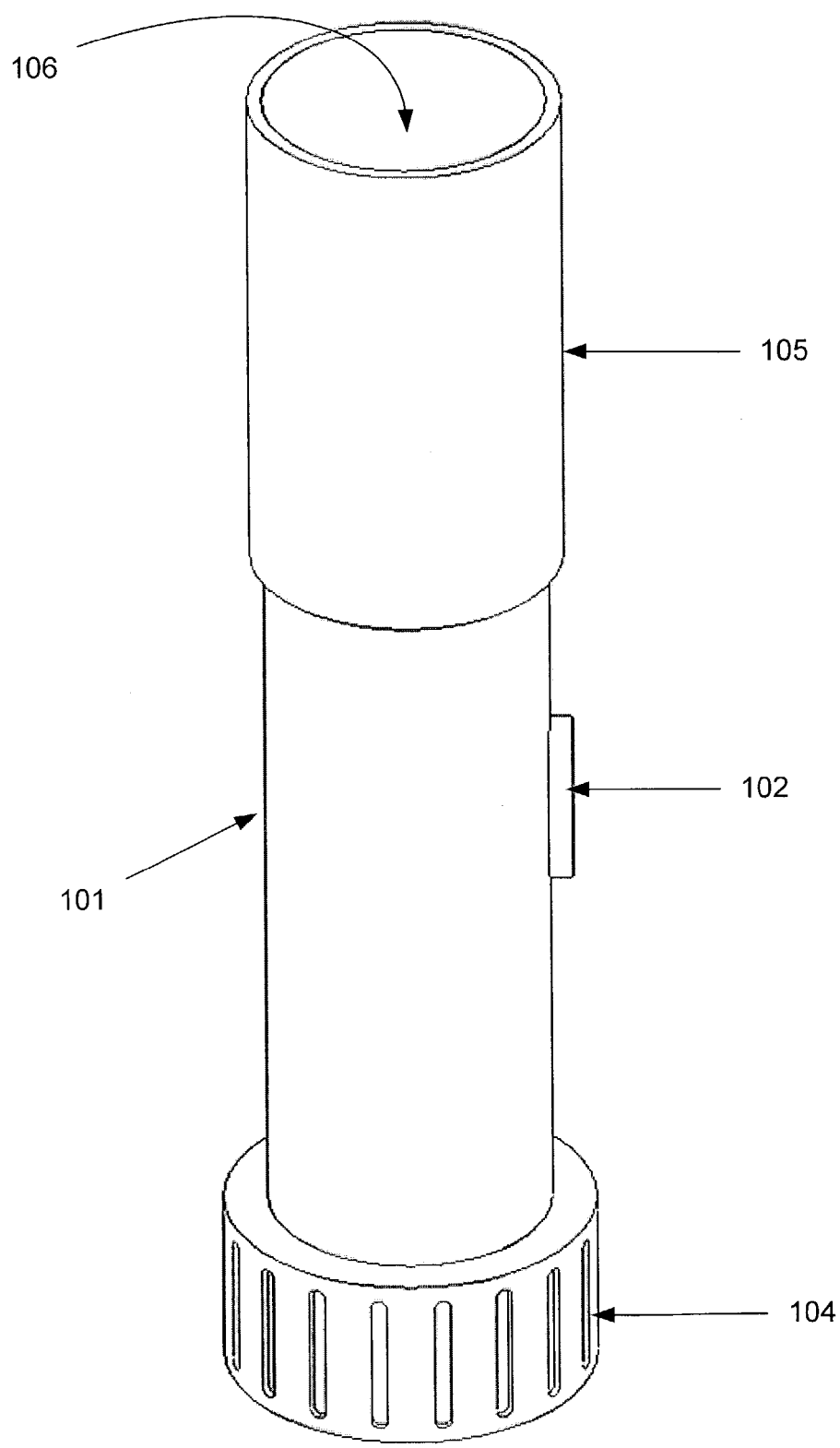
Figures 1, 3A:
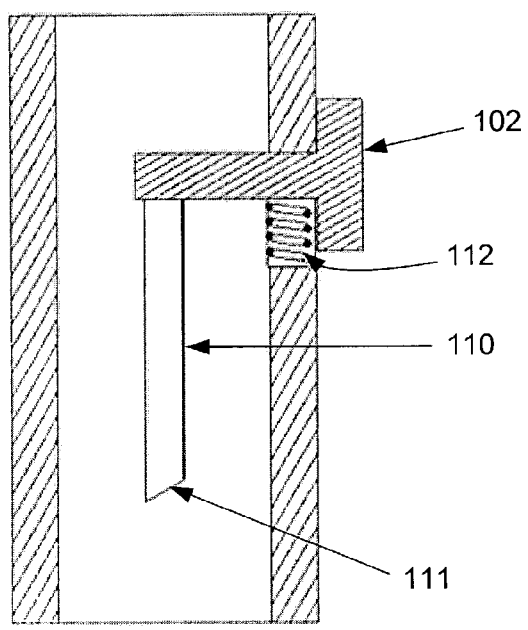

FIG. 1-*a* is a diagram illustrating a respiratory drug delivery system 100 in open position, according to one embodiment of the present invention. Respiratory drug delivery system 100 comprises a body 101 with a piercing trigger 102, and a cartridge 103. Cartridge 103 contains a drug, as well as a propellant for aerosolization of drug and respiratory delivery of drug to user. Optionally, cartridge 103 is mounted on or held by holder 104. FIG. 1-*b* illustrates respiratory drug delivery system 100 in closed position, according to one embodiment of the present invention.

Figures 2, 3A:
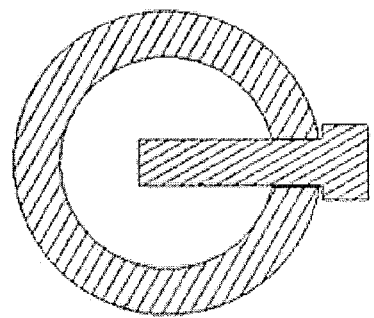
Figures 1, 3B:
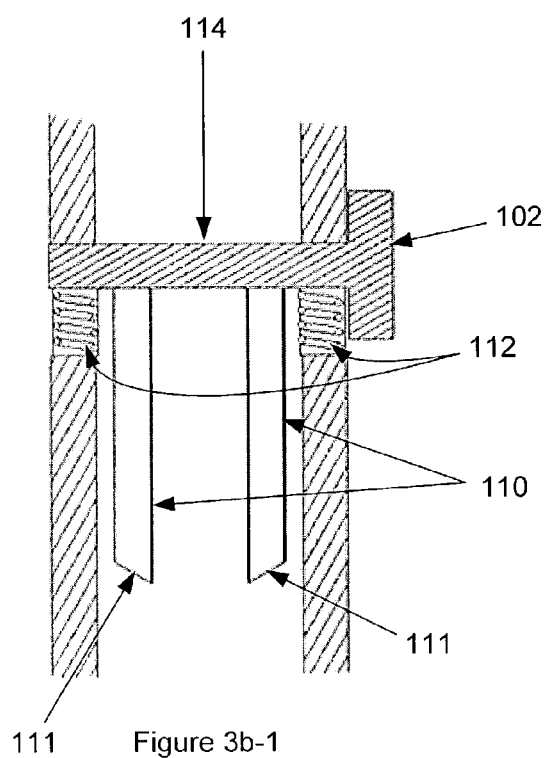
Figures 2, 3B:
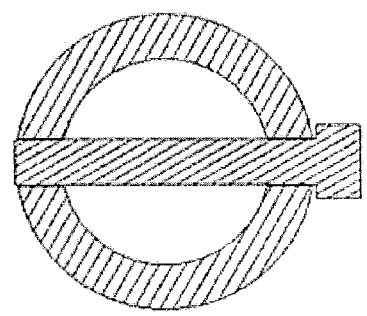
Figure 3C:
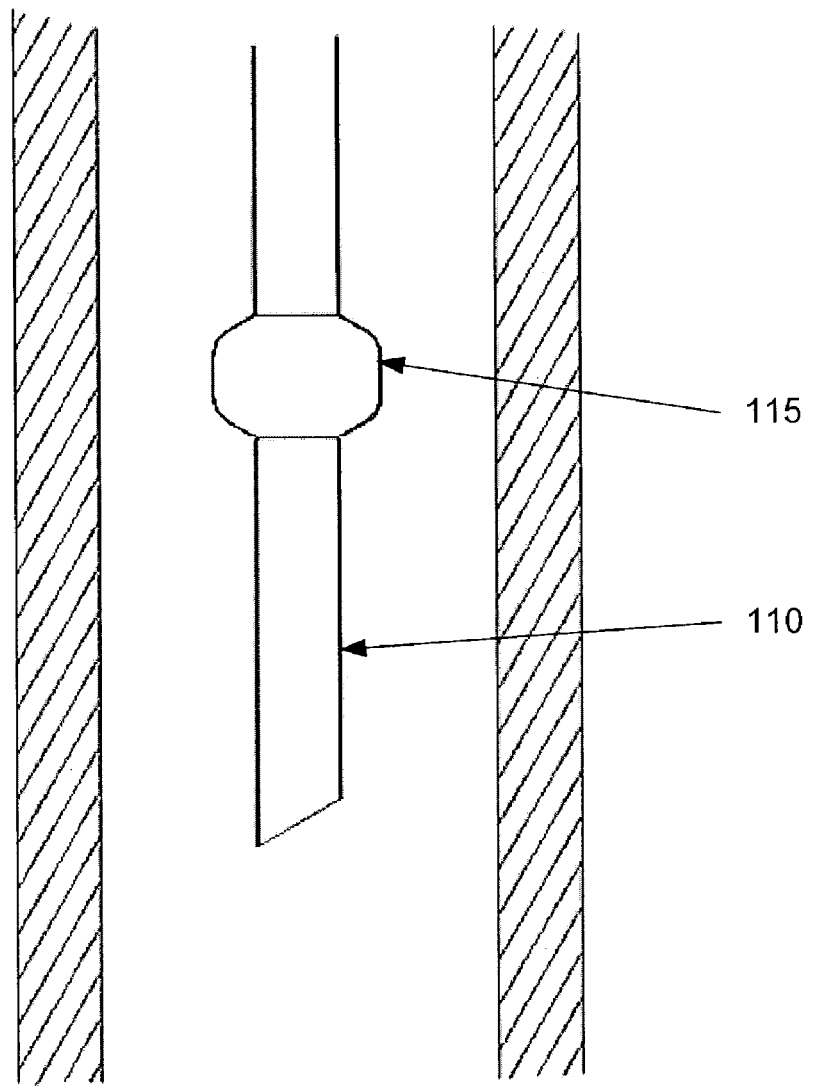
Figure 3D:
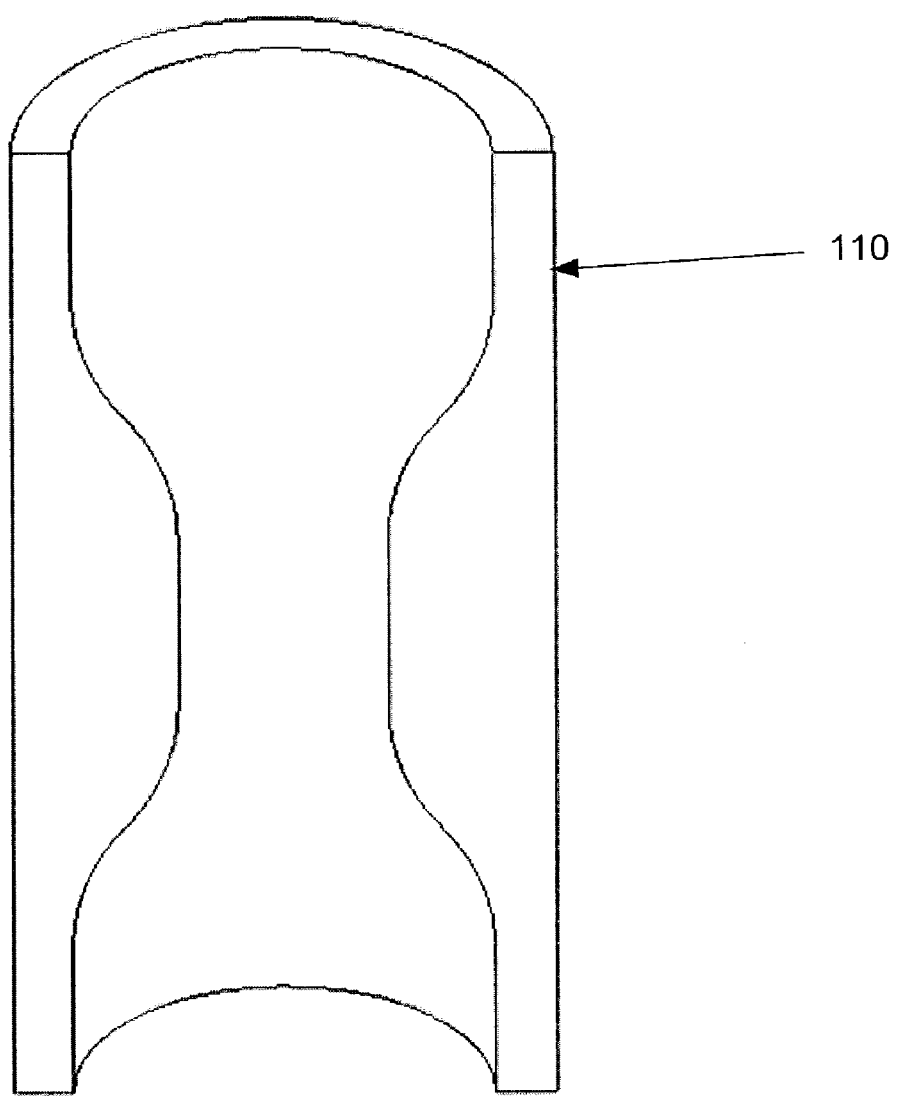
Figure 3E:
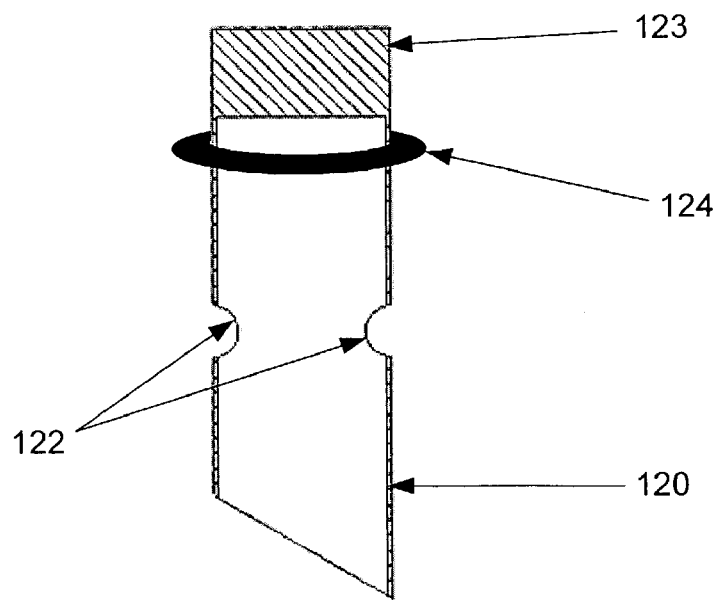
Figure 3F:
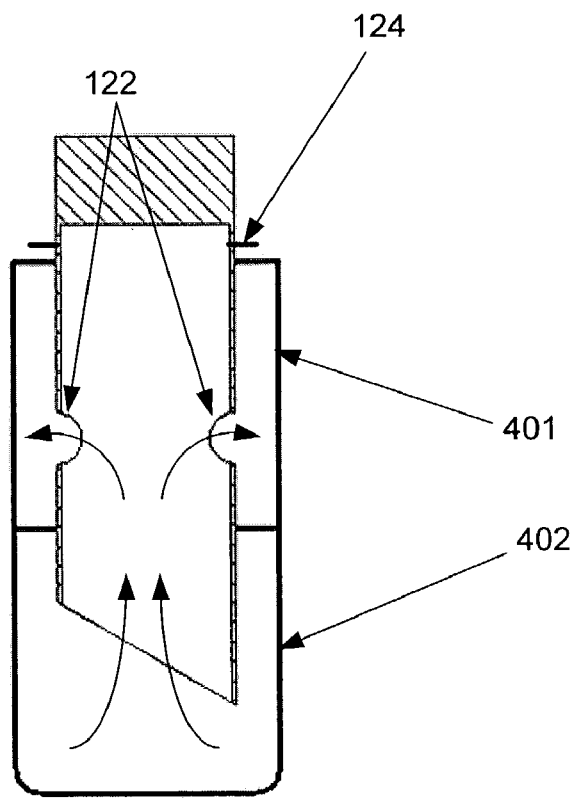
Figure 3G:
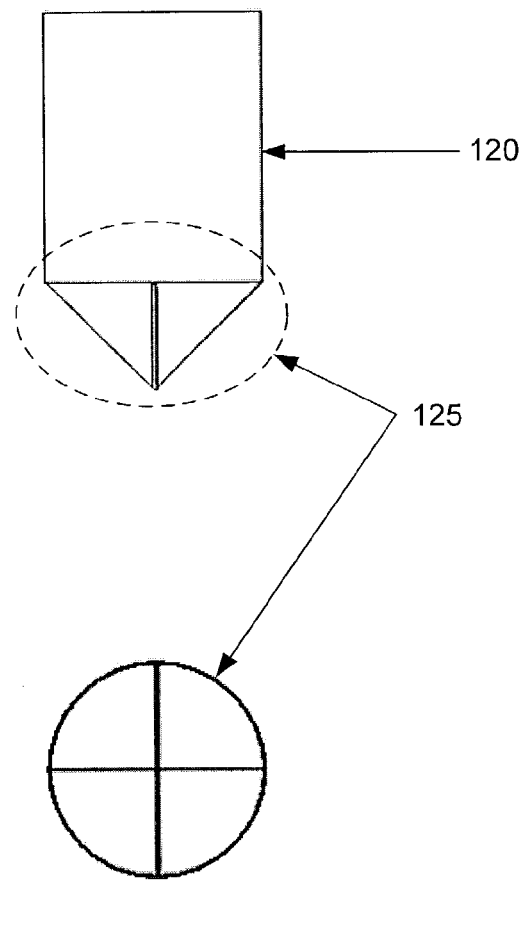
Figure 3G:
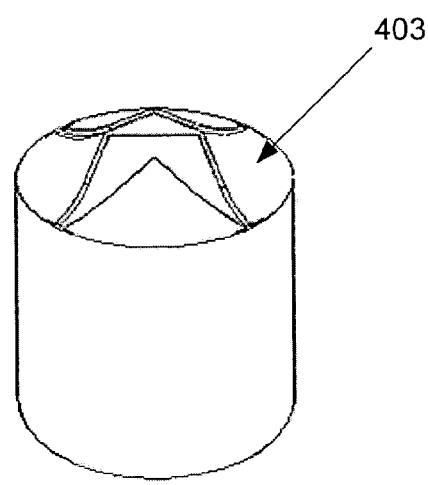
Figure 3H:
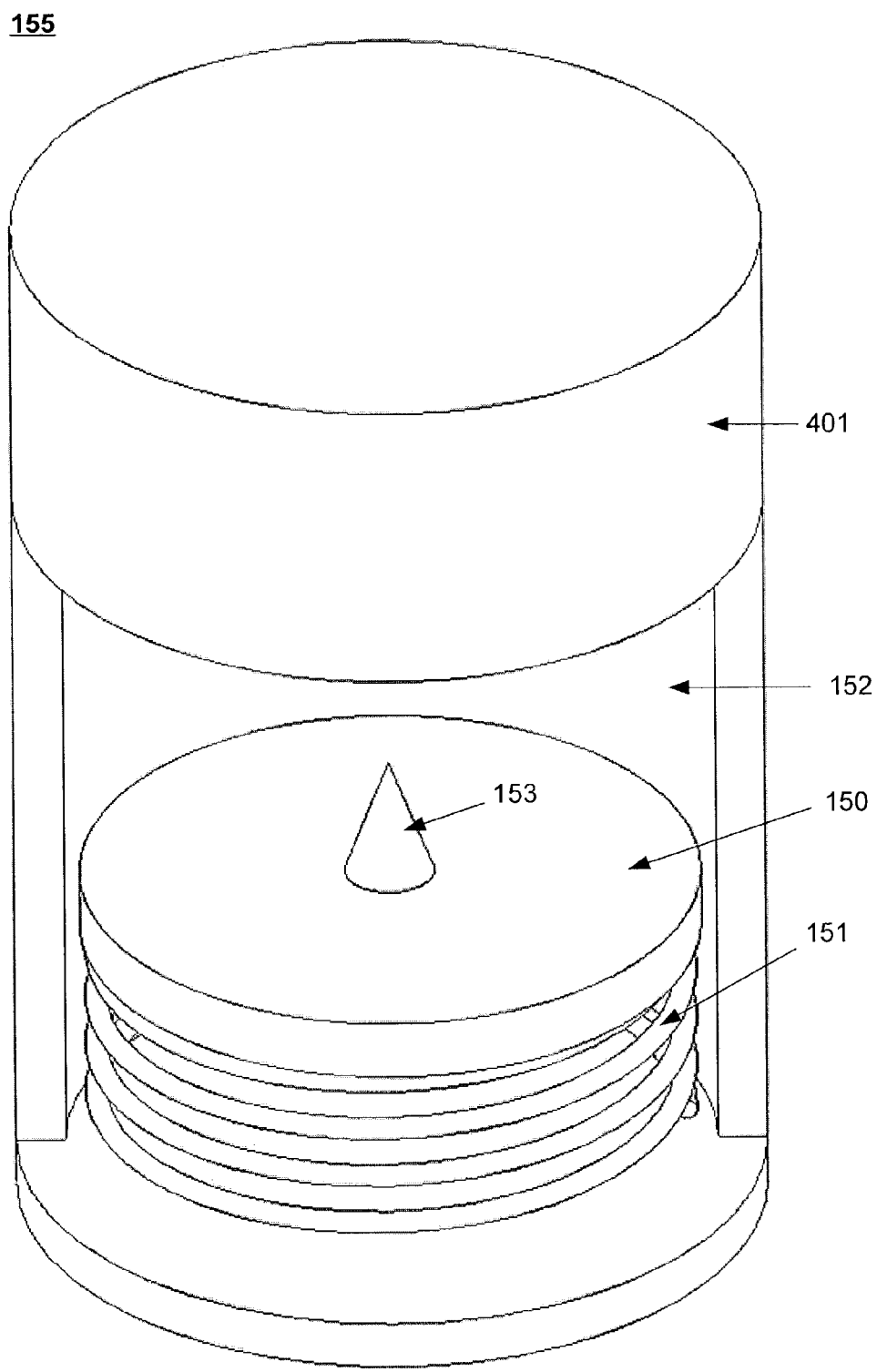
Figure 3I:
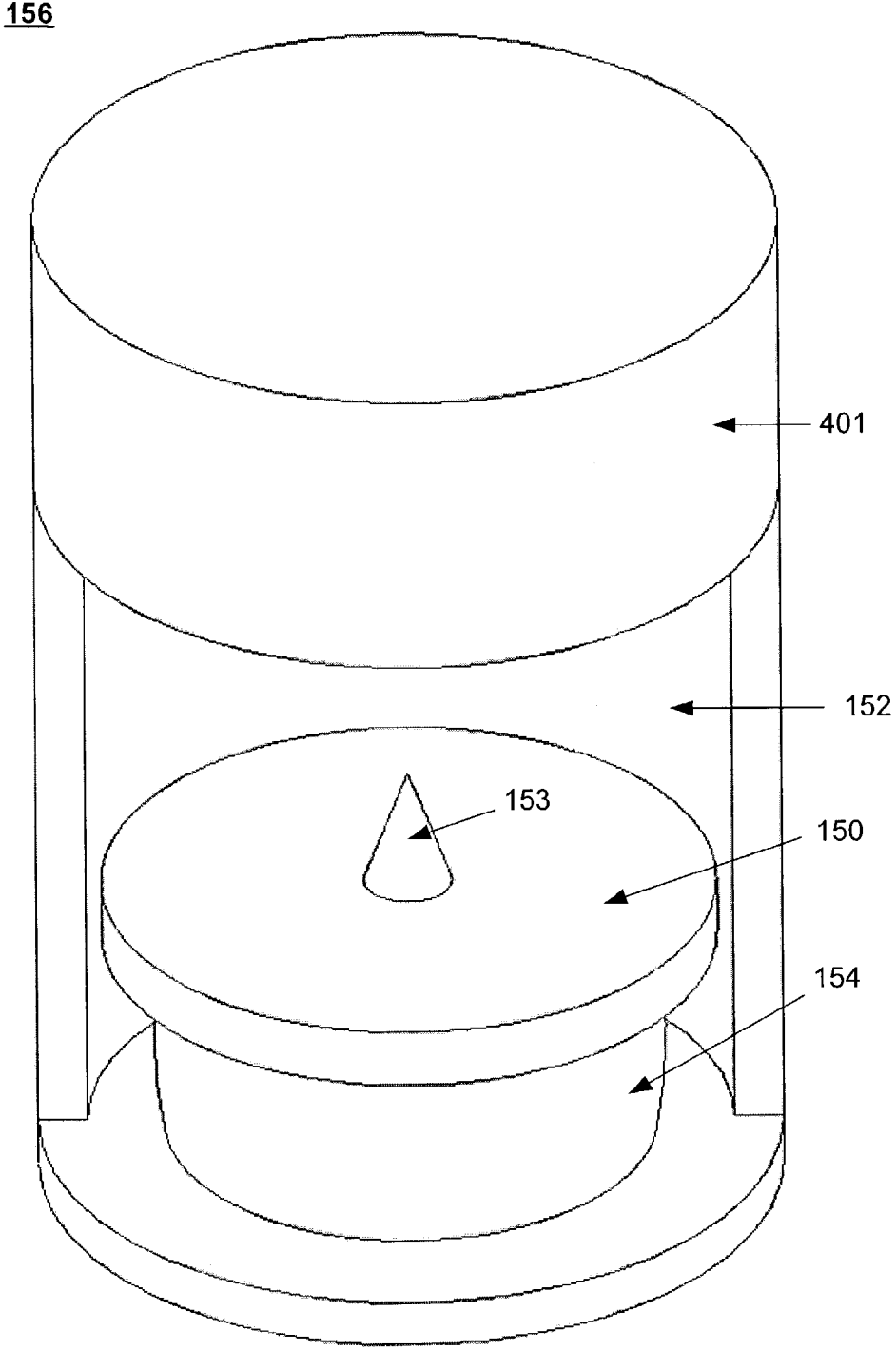
Figure 3J:
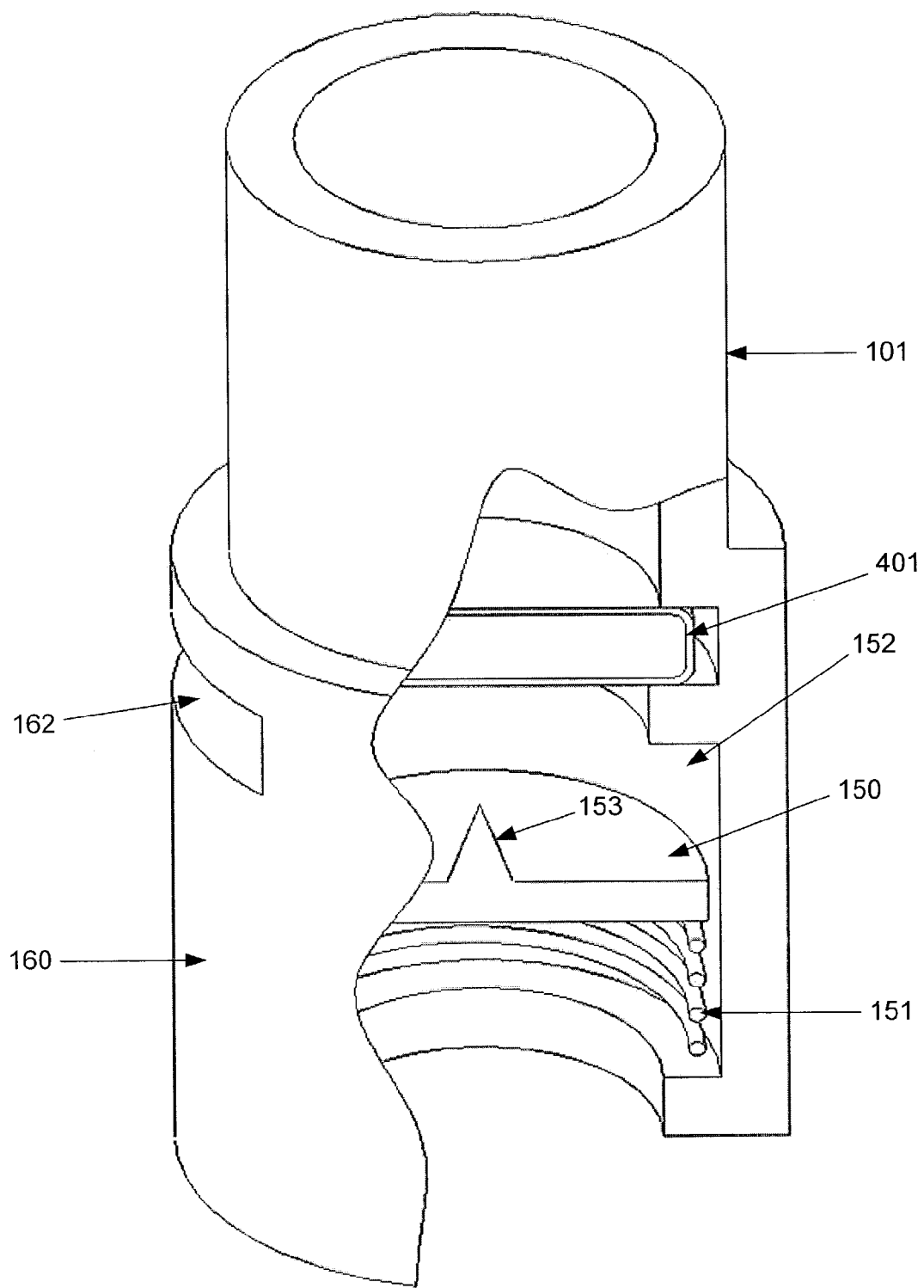
Figure 3K:
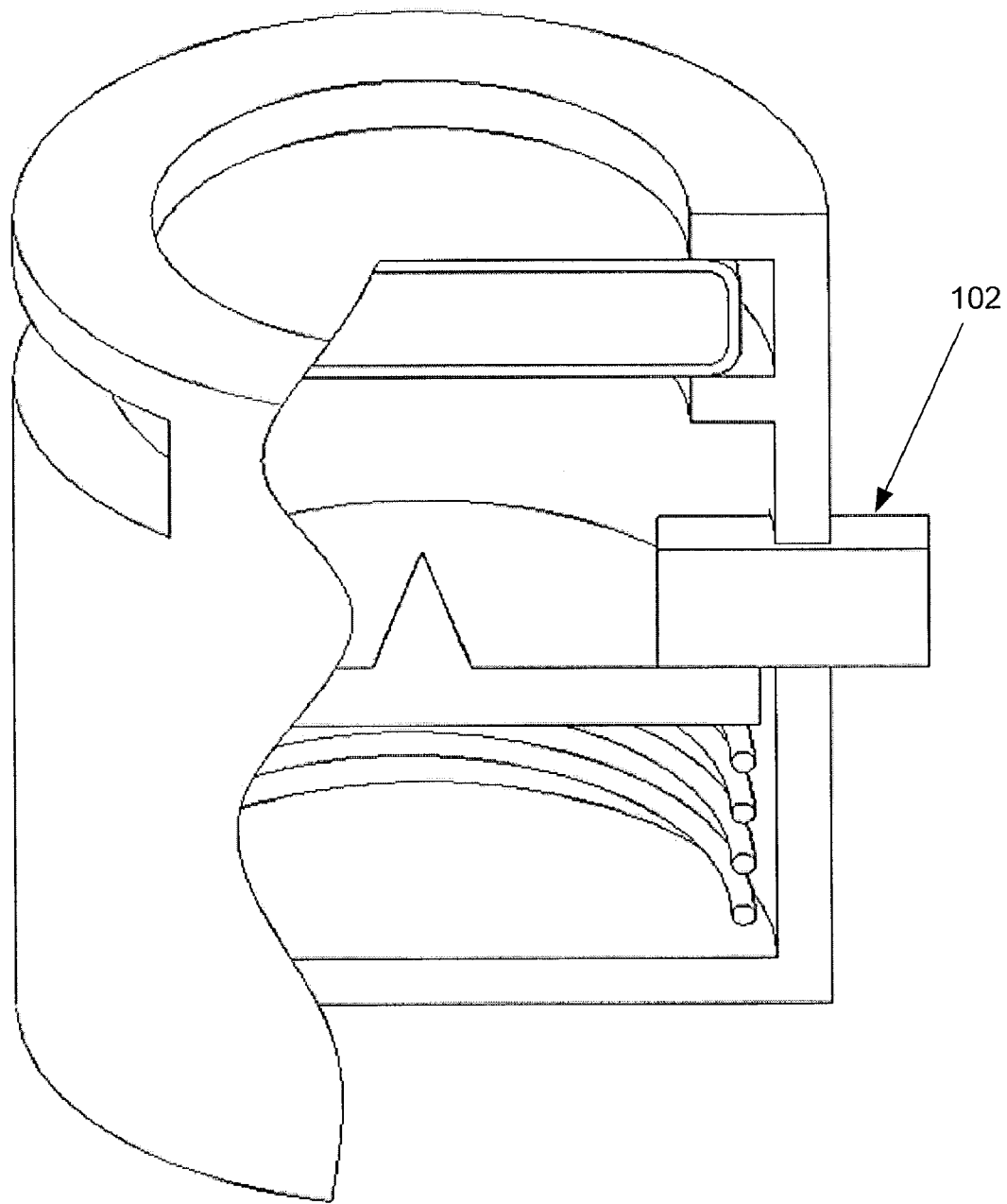

Body 101 comprises a mouthpiece 113 serving as inspiration opening for user. Mouthpiece 113 is the top end segment of body 101, or comprises a separate piece for coupling to top of body 101. Mouthpiece 113 is either a straight extension of body 101, or is shaped differently, for example as shown in FIGS. 2-*a*, 2-*b* or 2-*c*. FIG. 2-*a* is a diagram illustrating a tapered mouthpiece, according to one embodiment of the present invention. FIG. 2-*b* is a diagram illustrating a bent mouthpiece, according to another embodiment of the present invention. FIG. 2-*c* is a diagram illustrating a grooved mouthpiece, according to another embodiment of the present invention. For example user can bite on groove 201 to position mouth relative to mouthpiece 113 and hold steady for facilitating maximal drug delivery. Positioning of mouthpiece 113 affects flow dynamics and path of aerosolized drug for improved drug delivery to lungs and drug deposition. Different mouthpiece 101 shapes can be chosen by user for optimum comfort.

FIG. 2-*d* is a diagram illustrating a respiratory drug delivery system with optional spacer 105, according to one embodiment of the present invention. Spacer 105 comprises a mouthpiece 113 serving as inspiration opening for user (analogous to the mouthpiece for body 101 described above) with mouthpiece 113 as the top end part of spacer 105 or comprising a separate piece for coupling to top of spacer 105, as shown in FIGS. 2-*a*, 2-*b* or 2-*c*. Spacer 105 comprises a chamber 106 for storing an aerosolized drug prior to respiratory delivery. When using a spacer 105, mouthpiece 113 comprises a mechanism for holding the aerosolized drug within chamber 106 until user releases held aerosolized drug for respiratory delivery. In one embodiment, mouthpiece 113 comprises a lid and the user releases held aerosolized drug by activating a handle coupled to the lid. In another embodiment, the user releases held aerosolized drug by twisting the mouthpiece 113 to create an opening, wherein spacer 105 and mouthpiece 113 each comprise an opening at their common plane of contact, which openings can be either aligned for allowing a pathway for the aerosolized drug to travel from chamber 106 through mouthpiece 113, or misaligned for prohibiting travel of aerosolized drug.

FIGS. 3-*a*1 and 3-*a*2 are diagrams illustrating cross-section of a single-tubing piercing mechanism, according to one embodiment of the present invention. Pierce tubing 110 comprises opening 111. Spring 112 pushes pierce tubing 110 away from cartridge 103. Activating piercing trigger 102 moves pierce tubing 110 towards cartridge 103 for piercing cartridge 103. Pierce tubing 110 comprises plastic, metal, or other durable or disposable material. FIG. 3-*a*2 illustrates a top view of the single piercing mechanism.

Optionally, piercing mechanism and/or piercing trigger 102 are electrically powered, using a disposable or rechargeable battery or other power source.

FIGS. 3-*b*1 and 3-*b*2 are diagrams illustrating a cross-section of a multi-tubing piercing mechanism, according to one embodiment of the present invention. Two pierce tubings 110 are shown in the figure as examples. Other embodiments with additional pierce tubings 110 are analogous. The double-piercing mechanism depicted in FIG. 3-*b*1 comprises two pierce tubings 110, pushed away from cartridge 103 by springs 112. Pierce tubings 110 comprise openings 111, and are mounted on a ring shaped support structure 114. Pierce tubings 110 may be of different lengths, advantageously resulting in staggered cartridge piercing times (i.e. temporally offset or occurring sequentially) when trigger 102 is activated, for staggered drug aerosolization or drug delivery. FIG. 3-*b*2 illustrates a top view of the double-piercing mechanism.

FIG. 3-*c* is a diagram illustrating a cross-section of a bumped-piercing mechanism, according to one embodiment of the present invention. Pierce tubing 110 comprises bump 115 for staged aerosolization. Upon engaging trigger 102, the resistance of bump 115 accompanying the passing of bump 115 through a membrane of cartridge 103 indicates to the user that the membrane has been pierced. The first instance of resistance indicates piercing of the topmost membrane, the second instance of resistance indicating piercing of the membrane following the topmost membrane, and so forth. The user may thereby deduce when a drug is aerosolized and/or delivered and/or when to initiate a chaser. In addition, some drugs have no taste, making it difficult for a user to know whether the drug has been delivered or not, and bump 115 can indicate drug delivery in such cases.

FIG. 3-*d* is a diagram illustrating necked interior cross-section of pierce tubing 110, according to one embodiment of the present invention. The necked design improves velocity of propellant (released from propellant compartment) through pierce tubing 110 for achieving improved propellant flow (for example sonic or hyper-sonic flow) for improved mixing of drug with propellant or for improved mixing of different drugs coming from different drug compartments. Alternatively, pierce tubing 110 does not have necked interior cross-section, but has simple cylindrical interior.

FIG. 3-*e* is a diagram illustrating detail of pierce head, according to one embodiment of the present invention. The head 120 of pierce tubing 110 is hollow with openings 122 on the side, and cross-section 123 is closed to prevent propellant flow beyond cross-section 123. Stopper ring 124 stops piercing movement of pierce tubing 110 through membrane 403 for proper positioning of openings 122 and for preventing openings 122 to cross membrane 403 into the propellant compartment. Stopper ring 124 may also serve as a seal, preventing leakage of drug or aerosolized drug from drug compartment 401 into body 101.

FIG. 3-*f* is a diagram showing simulation of air and drug flow through pierce tubing 110, according to one embodiment of the present invention. When pierce head 120 of pierce tubing 110 pierces propellant compartment 402, the pressure in propellant compartment 402 causes the propellant to flow through pierce head 120 and out through openings 122 into the drug compartment 401. This provides mixing of propellant with drug and/or de-agglomeration of drug, for increased rate and/or efficiency of drug delivery. Upon release of piercing trigger 102, pierce tubing 110 retracts from propellant compartment 402 and from drug compartment 401, providing an opening for the flow of aerosolized drug into body 101 and to user.

In an alternative embodiment, pierce tubing 110 is hollow over its entire length, with an opening at the top of pierce tubing 110. Pierce tubing head 120 pierces drug compartment 401, collecting into the hollow pierce tubing 110 an amount of the drug in drug compartment 401. Subsequent piercing of propellant compartment 402 causes the propellant to flow through pierce tubing 110, and mix with and/or aerosolize the drug collected in pierce tubing 110. Propellant and drug then travel out through the opening at the top of pierce tubing 110 and into body 101 for respiratory delivery. Pierce tubing 110 may comprise a large diameter for collecting sufficient amount of drug into the hollow pierce tubing 110 (for example an external diameter close to the internal diameter of the pierced compartments).

FIGS. 3-g1, 3-g2 and 3-g3 are diagrams illustrating a pierce tip of the pierce head and corresponding membrane puncture, according to one embodiment of the present invention. FIG. 3-g1 shows pierce head 120 having pierce tip 125 with cross-section as shown in FIG. 3-g2. Upon piercing a membrane 403, pierce tip 125 produces pie like puncture and opening as shown, with flaps opening away as forced by outward flow of propellant or aerosolized drug. Alternatively, pierce tip 125 comprises pierce head 125 with tapered opening similar in shape to a syringe needle opening, producing a circular or round cut in membrane 403 opening away as forced by outward flow of propellant or aerosolized drug.

FIG. 3-h is a diagram illustrating a disposable cartridge 155 with spring-loaded plunger mechanism, according to one embodiment of the present invention. Plunger 150 is mounted on loaded spring 151 at the bottom of chamber 152. Plunger 150 has pierce head 153 for piercing drug compartment 401. Chamber 152 contains a propellant, wherein the propellant may or may not be pressurized. After releasing loaded spring 151 (for example by activating a release lever coupled to piercing trigger 102, or by activating a trigger mounted on the disposable cartridge 155 itself, or by using another mechanism for releasing loaded spring 151), spring 151 thrusts plunger 150 upwards, piercing drug compartment 401 with pierce head 153, thrusting propellant into drug compartment 401 and aerosolizing drug for respiratory delivery.

FIG. 3-i is a diagram illustrating a disposable cartridge 156 with compressed-elastomer plunger mechanism, according to one embodiment of the present invention. Plunger 150 is mounted on compressed elastomer 154 at the bottom of chamber 152. Plunger 150 has pierce head 153 for piercing drug compartment 401. Chamber 152 contains a propellant, wherein the propellant may or may not be pressurized. After releasing compressed elastomer 154 (for example by activating a release lever coupled to piercing trigger 102, or by activating a trigger mounted on the disposable cartridge 156 itself, or by using another mechanism for releasing compressed elastomer 154), compressed elastomer 154 thrusts plunger 150 upwards, piercing drug compartment 401 with pierce head 153, thrusting propellant into drug compartment 401 and aerosolizing drug for respiratory delivery.

FIG. 3-j is a diagram illustrating a reusable cartridge 160 with spring-loaded plunger mechanism, according to one embodiment of the present invention. Reusable cartridge 160 is permanently coupled to body 101 and has slot 162 for inserting a drug compartment 401. Plunger 150 is mounted on loaded spring 151 at the bottom of chamber 152. Plunger 150 has pierce head 153 for piercing inserted drug compartment 401. Chamber 152 contains a propellant, wherein the propellant may or may not be pressurized. After releasing loaded spring 151 (for example by activating a release lever coupled to piercing trigger 102, or by activating a trigger mounted on the reusable cartridge 160 itself, or by using another mechanism for releasing loaded spring 151), spring 151 thrusts plunger 150 upwards, piercing drug compartment 401 with pierce head 153, thrusting propellant into drug compartment 401 and aerosolizing drug for respiratory delivery. Alternatively, reusable cartridge 160 is not permanently coupled to body 101, but allows coupling of body 101 onto top of cartridge 160 when in use and allows for removal of body 101 from cartridge 160 when not in use, as shown in FIG. 3-k.

FIG. 4-a is a diagram illustrating a drug cartridge 103 with one drug compartment 401 and one propellant compartment 402. Compartments 401 and 402 are separated by membrane 403. Compartment 401 contains a drug, such as Albuterol, Budesonide, Insulin, or other powdered drug for respiratory delivery. Compartment 402 contains a propellant. Propellant in compartment 402 is pressurized, for example at a pressure of 1 psi to 50 psi. A pressure below 1 psi or above 50 psi may be used, for example for a user with low inspiratory flow rate such as a pediatric patient or a cystic fibrosis patient, or for a user with high inspiratory flow rate such as an athlete, or for a user with low or high lung capacity, for providing comfort and maximal drug deposition. Cartridge 103 material comprises single-layer or multi-layer plastic or metallic material, or other material for containing drug and/or propellant.

Figure 4A:
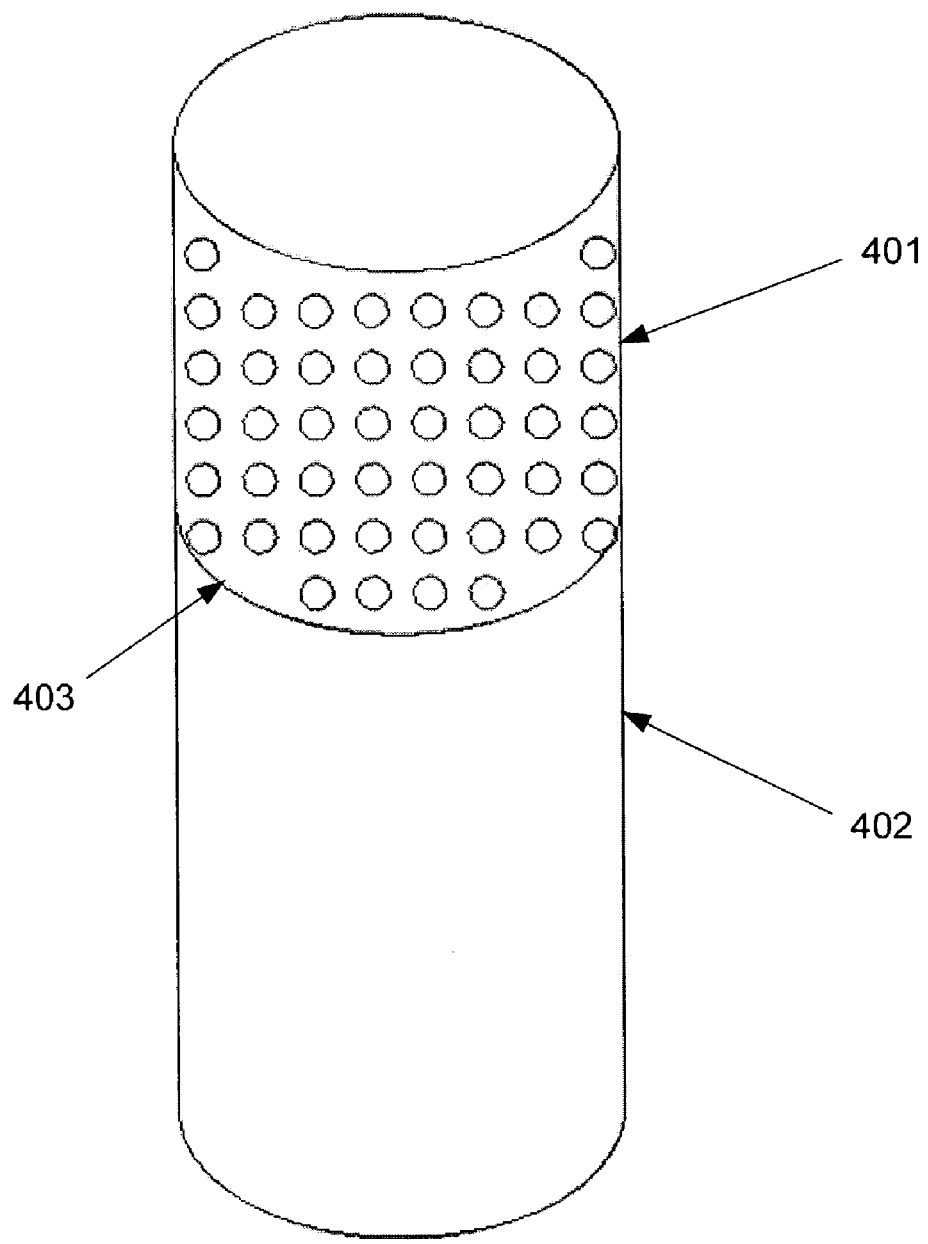
Figure 4B:
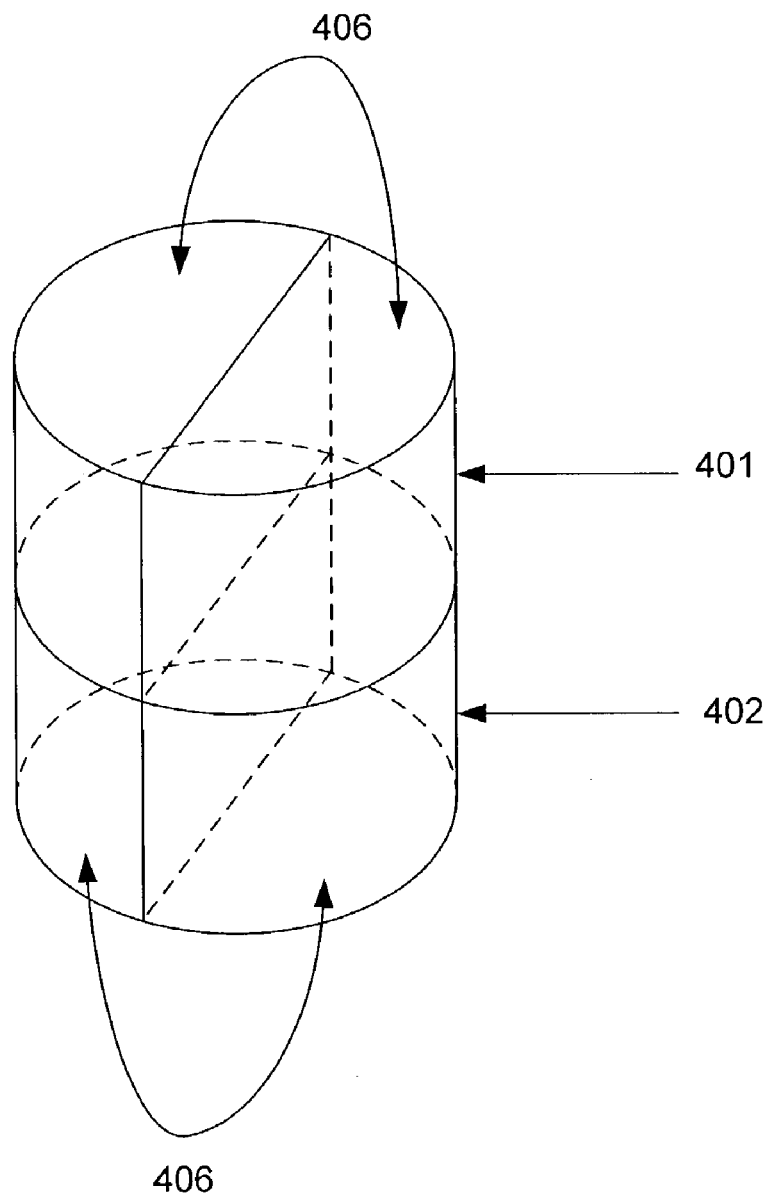
Figure 4C:
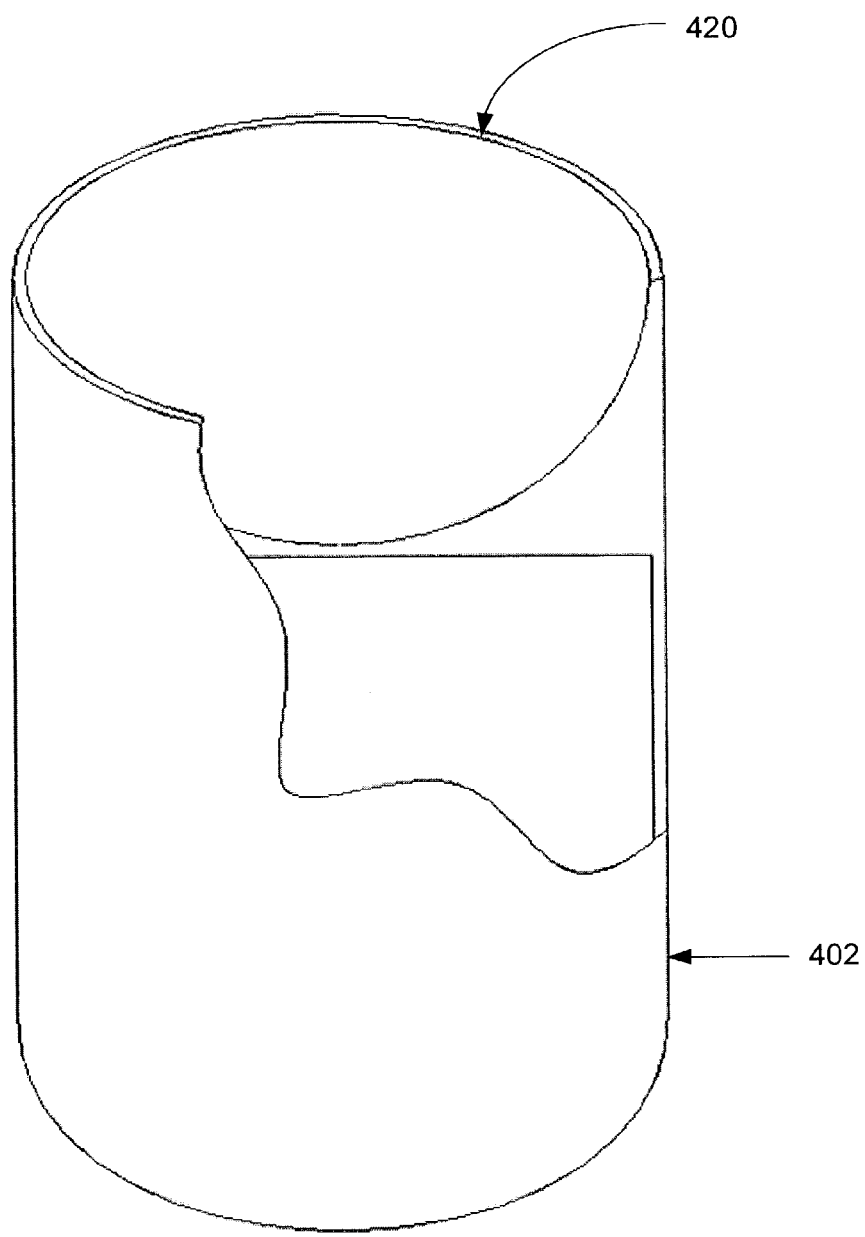
Figure 4D:
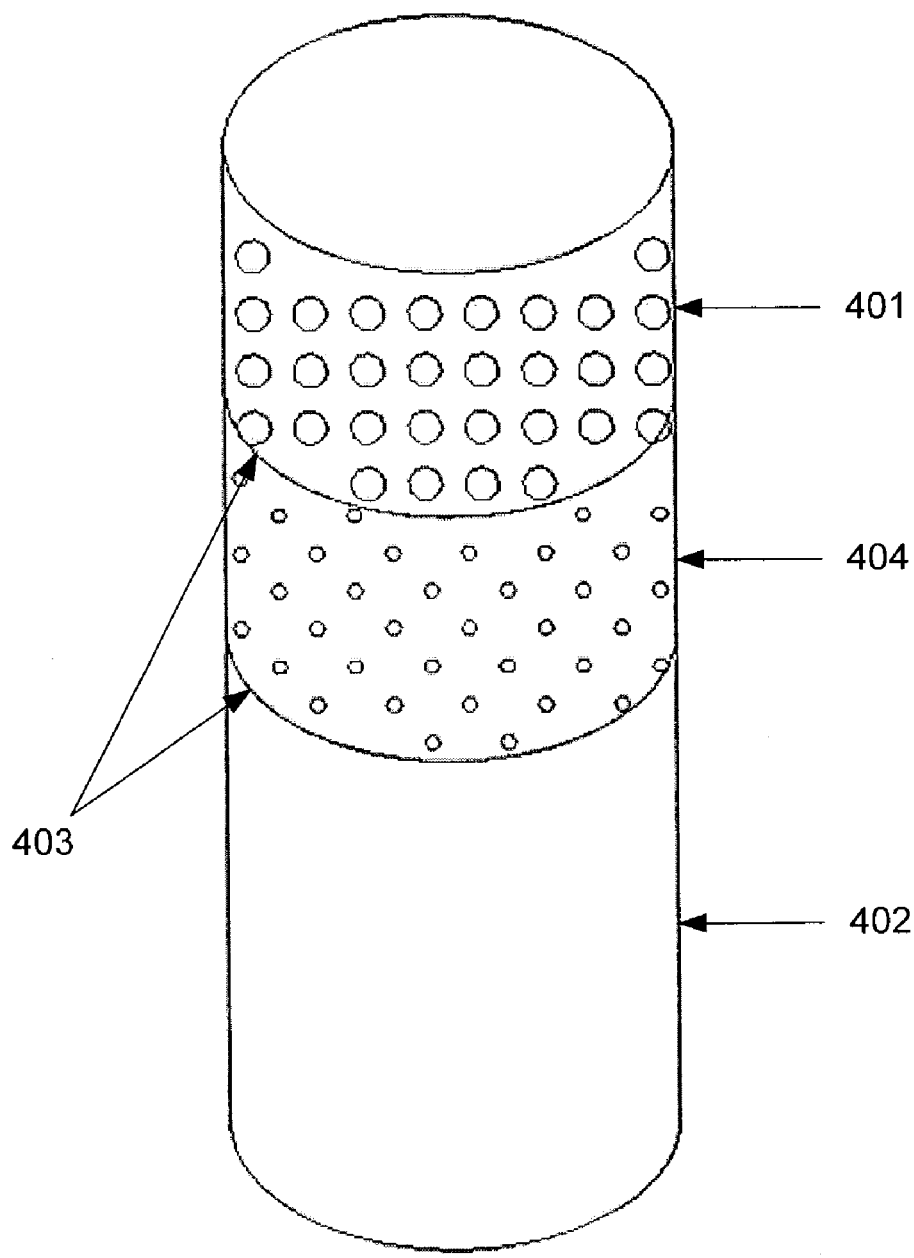
Figure 4E:
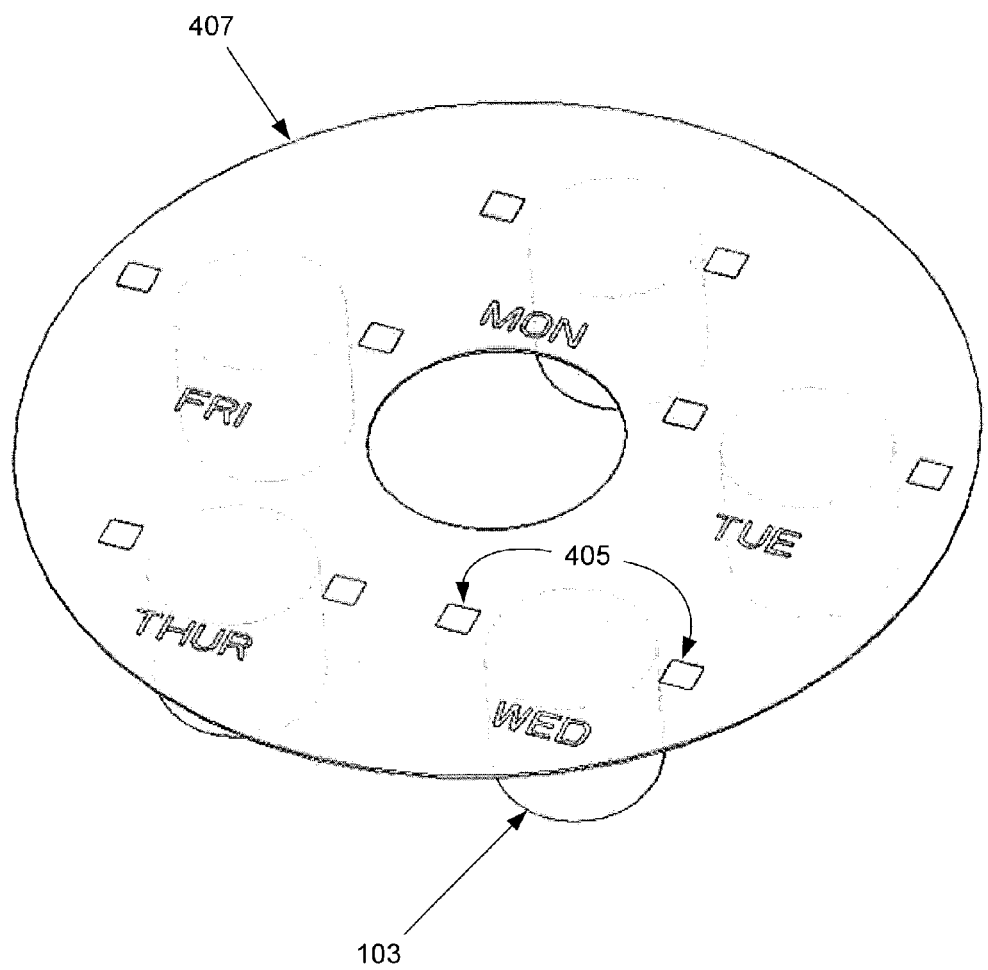
Figure 4F:
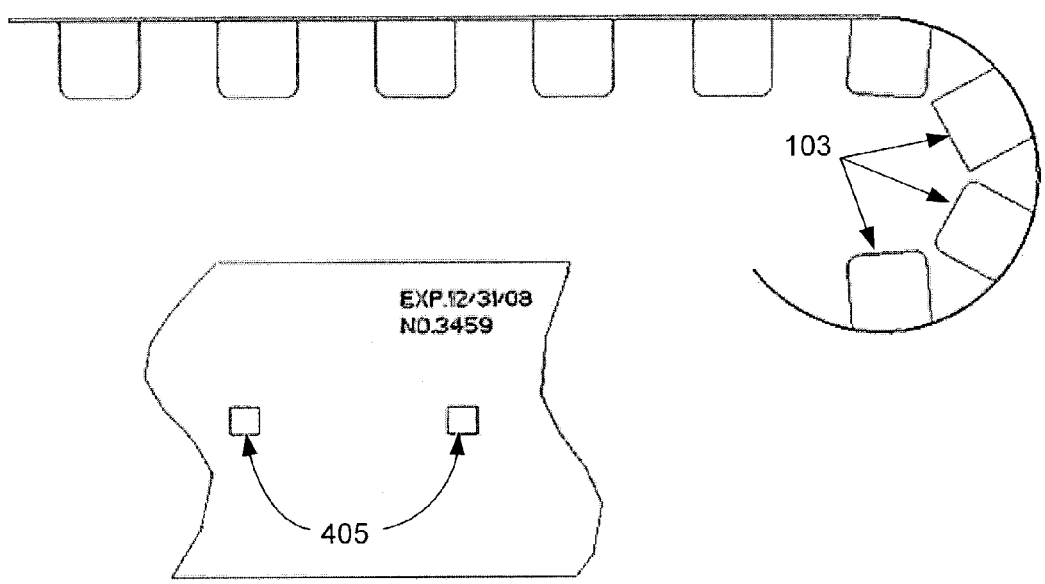
Figure 4G:
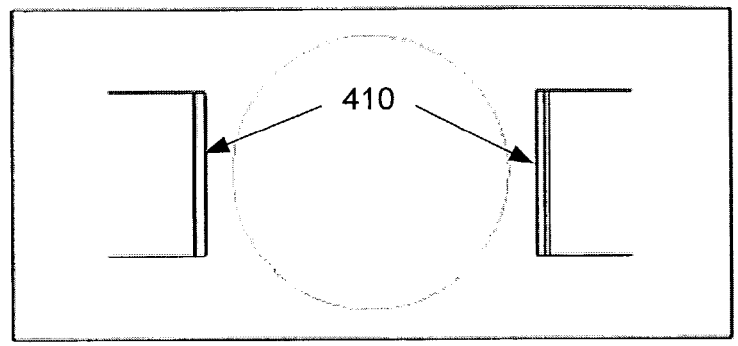
Figure 4G:
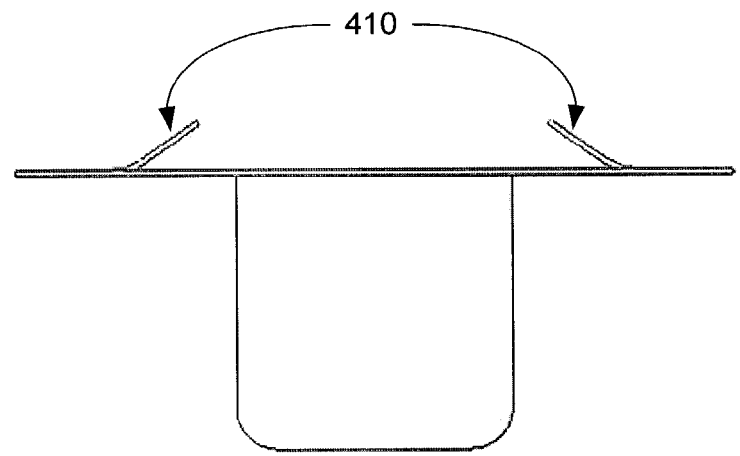
Figure 4G:
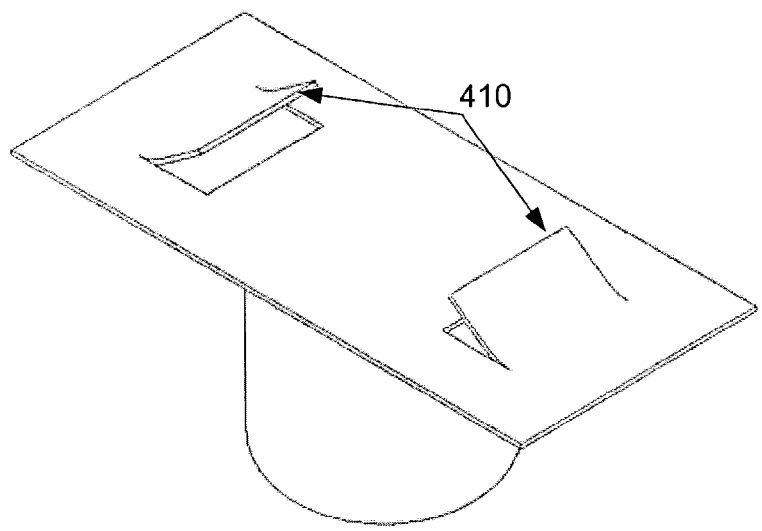

Optionally, drug compartment 401 and/or propellant compartment 402 are divided into sub-compartments 406, as shown in FIG. 4b. The staggered multi-tubing piercing mechanism described above operates in conjunction with a partitioned drug compartment 401 and partitioned propellant compartment 402. The drug residing in the drug sub-compartment 406 corresponding to the longer pierce tubing 110 is pierced, aerosolized and delivered first, followed by the drug residing in the drug sub-compartment 406 corresponding to the shorter pierce tubing 110, resulting in overall staggered drug delivery, useful for users who take drugs to be delivered in staggered fashion. Optionally, partitioned drug compartments 401 and/or propellant compartments 402 operate in conjunction with non-staggered multi-tubing pierce mechanism for simultaneous delivery of drugs which are to be stored separately (in separate sub-compartments 406) to avoid mixing prior to aerosolization. Optionally, drug compartments and/or propellant compartments are divided into more than two sub-compartments 406, operating in conjunction with staggered or non-staggered multi-tubing pierce mechanisms.

FIG. 4-c is a diagram illustrating a drug cartridge with a drug reservoir, according to one embodiment of the present invention. Drug reservoir 420 allows for placement of one or more drug packages (such as a drug capsule, a drug blister package or other package containing a drug) above propellant compartment 402. Activating piercing trigger 102 will move pierce tubing 110 towards drug package placed in drug reservoir 420, and the piercing of drug package followed by the piercing of propellant compartment 402 aerosolizes the drug for respiratory delivery. Optionally, reservoir 420 allows for placement of drug powder, or other substance to be aerosolized, directly into reservoir 420, for subsequent piercing of propellant compartment 402 and aerosolization of said drug powder or other substance. For example, user can take a capsule containing a drug powder, empty the contents of the capsule into drug reservoir 420, and aerosolize drug powder by activating piercing trigger 102 and piercing propellant compartment 402, resulting in respiratory delivery of drug.

FIG. 4-d is a diagram illustrating a drug cartridge with two drug compartments and one gas compartment. Compartments 401, 404, and 402 are separated by membranes 403. In one embodiment, compartments 401 and 404 contain drugs, while compartment 402 contains a propellant as described above. The drug in compartment 401 may be different from the drug in compartment 404, and the two drugs may be unsuitable for mixed storage, but may require mixing when delivered to user. In another embodiment, compartment 401 contains a drug, compartment 404 contains a propellant, and compartment 402 contains a chaser, with the compartments separated by membranes 403. Alternatively, cartridge comprises multiple drug and/or propellant and/or chaser compartments stacked in an order according to any desired sequence of piercing, drug aerosolization and respiratory drug delivery.

Optionally, cartridge 103 has one compartment only, for example containing Oxygen, Nitrous Oxide, other gas or substance, or combination of gases, for respiratory delivery. Alternatively, and for improved delivery and/or deposition of said contents, cartridge 103 has an additional compartment containing a chaser.

FIG. 4-e is a diagram illustrating a multi-dose rotary cartridge configuration, according to one embodiment of the present invention. Multiple cartridges 103 are assembled in weekly, monthly or other regular dosing in rotary configuration 407. Optional opening 405 provides opening for mounting body 101 on rotary configuration 407. Shape, size or location of opening 405, or distance between two or more openings 405, serve as key for mounting matching body 101. In one embodiment, opening 405 and body 101 are drug specific, such that only an appropriate body 101 and keyed cartridge 103 pair will fit to deliver a specific drug to a user in possession of the appropriate body/cartridge combination. In another embodiment, body 101 or opening 405 are age-group specific (such as for children or adults), user specific (such as for a specific person), or specific to other user attribute for limiting use to users with said attribute, or for serving as safety feature preventing accidental or intentional misuse of drug cartridge 103.

FIG. 4-f is a diagram illustrating a roll-up linear cartridge configuration, according to one embodiment of the present invention. Cartridges 103 are assembled in a multi-cartridge roll-up configuration. Optional keyed detail 405 provides mounting point for appropriate body 101, with optional drug specific keyed detail 405 and body 101 as described above.

FIG. 4-g is a diagram illustrating a cartridge configuration with flow resistance flaps 410, according to one embodiment of the present invention. Flexibility and/or surface area of flaps 410 provides inspiratory flow resistance resulting in maximal drug deposition through inspiration by user. Optionally, cartridge 103 comprises flaps 410 with pre-configured flexibility and/or according to user need, for example less flexible flaps 410 for adults and more flexible flaps 410 for children (who have lower lung capacity compared to adults).

Figure 5A:
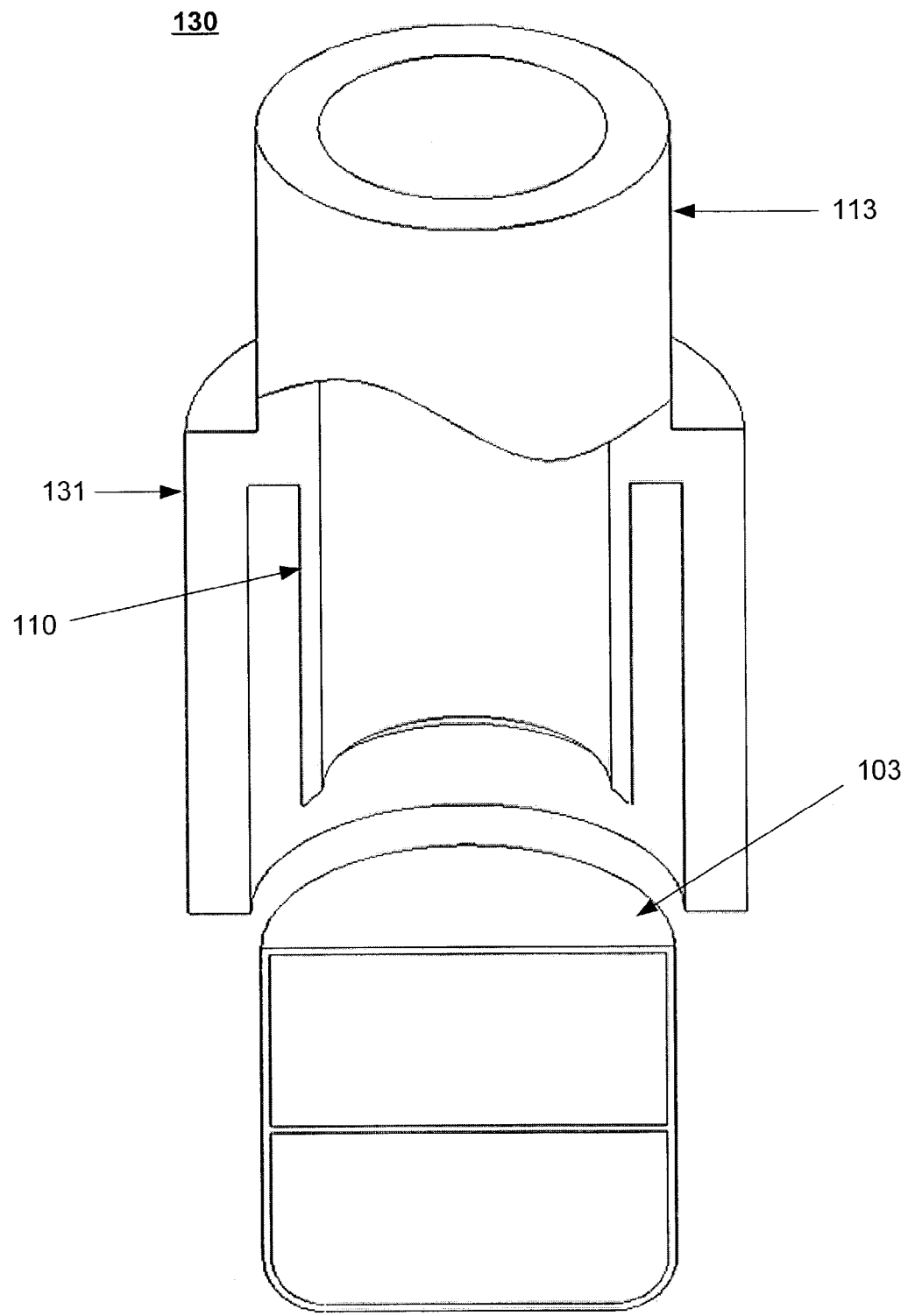
Figure 5B:
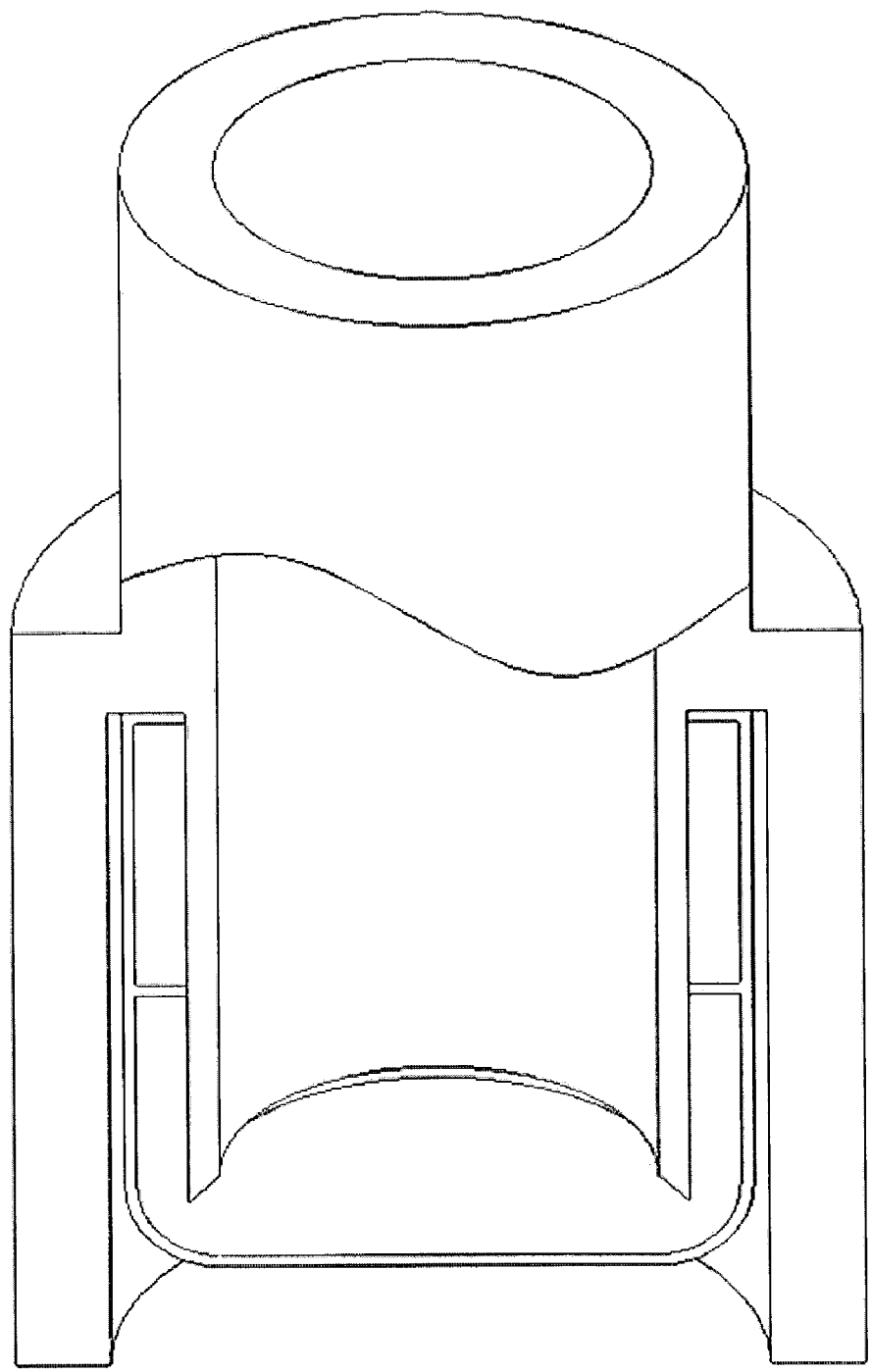

FIG. 5-a is a diagram illustrating a micro-version 130 of the respiratory drug delivery system, according to one embodiment of the present invention. The micro-version 130 does not have a separate piercing trigger. Instead, the body 131 contains the piercing mechanism with one or more tubings 110 at one end of the body and as shown in FIG. 5-a. User pushes cartridge 103 and body 131 against each other while holding mouth to other end of body 131 serving as mouthpiece 113, resulting in piercing of the cartridge 103 compartments by pierce tubing 110 and subsequent respiratory delivery of drug. The micro-version 130 is suitable for use in environments demanding a compact drug delivery system, such as for soldiers in battle or for mountain climbers with minimal space for carrying equipment. FIG. 5-b shows the micro version 130 of the respiratory drug delivery system piercing drug cartridge 103.

Figure 6:
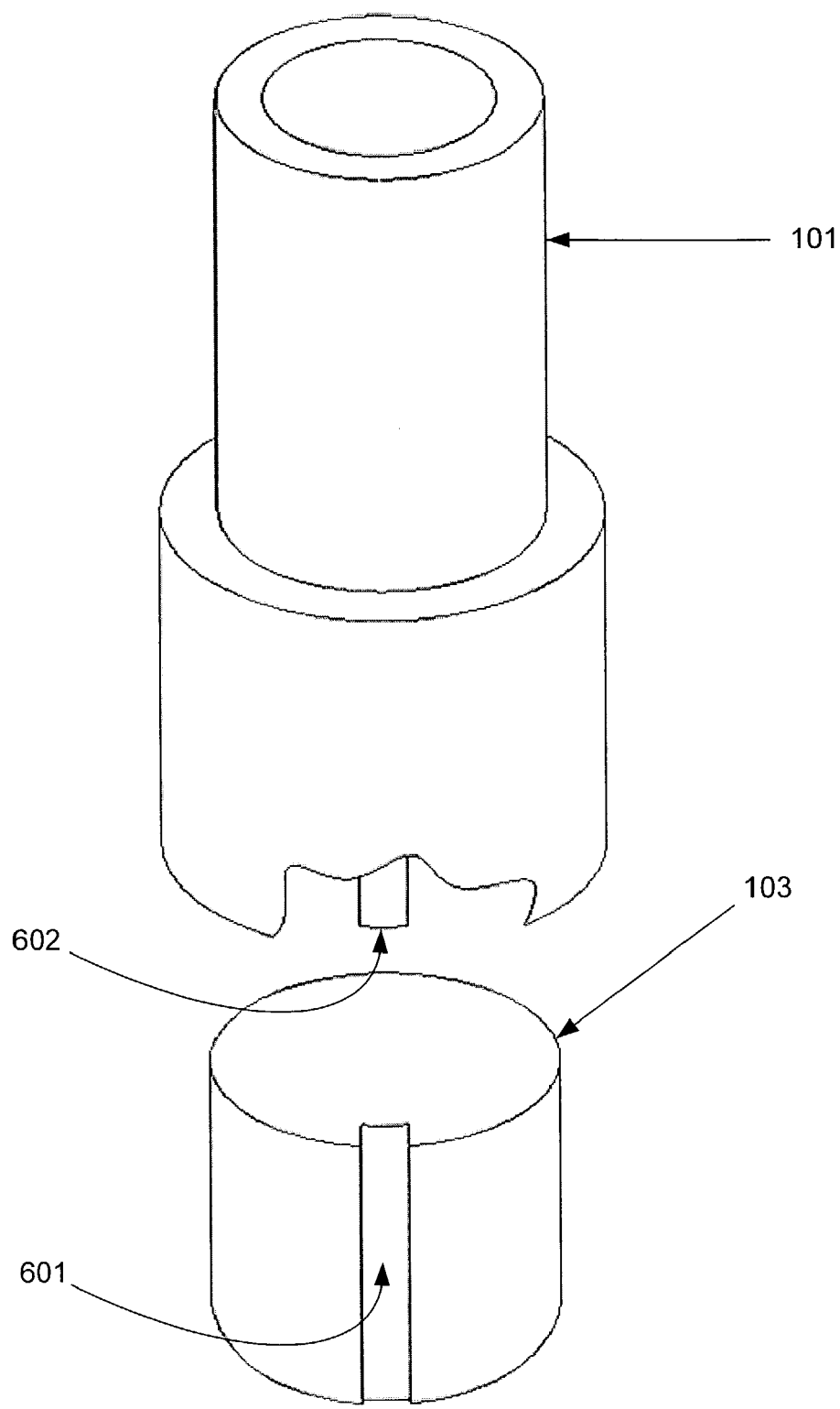

FIG. 6 is a diagram illustrating optional locators on drug cartridge 103, according to one embodiment of the present invention. Optionally, drug cartridge 103 has one or more cartridge locators 601 to aid in properly aligning body 101 (and/or micro-version body 131) with drug cartridge 103 for piercing, using one or more corresponding body locators 602. Cartridge locators 601 are optionally drug specific. Varying the number and/or shape and/or size of cartridge locators 601 and/or the spacing between cartridge locators 601 results in a "key" which must be matched by corresponding body locators 602 on body 101 (or on micro-version body 131) for proper alignment and piercing of cartridge 103. This key can be drug specific, age-group specific (such as for children or adults), user specific (such as for a specific person), or specific to other user attribute for limiting use to users possessing said attribute, or for serving as safety feature preventing accidental or intentional misuse of drug cartridge 103. For example, a child having her own respiratory drug delivery system with properly keyed body 101 (i.e. keyed for children) is prevented from using an adult drug cartridge 103 if the adult drug cartridge 103 is properly keyed for adults.

FIG. 7 is a flow chart illustrating a method for respiratory drug delivery, according to one embodiment of the present invention. Place 701 cartridge 103 in the respiratory drug delivery system 100. Activate piercing trigger 102 to pierce 702 drug compartment 401 and to pierce 703 propellant compartment 402, resulting in aerosolization and de-agglomeration of drug and respiratory delivery 704 of drug.

Step 701 may be optional or unnecessary if the respiratory drug delivery system is pre-packaged with a cartridge 103 (for example at time of manufacturing or distribution), such as for example a disposable respiratory drug delivery system or a respiratory drug delivery system prepared (i.e. pre-loaded with a cartridge 103) for a user by a nurse, a health care provider, a doctor or other service provider.

Foregoing described embodiments of the invention are provided as illustrations and descriptions. They are not intended to limit the invention to precise form described. Other variations and embodiments are possible in light of above teachings, and it is thus intended that the scope of invention not be limited by this Detailed Description, but rather by claims following.

What is claimed is:

1. A respiratory drug delivery system, comprising:
   a body;
   a piercing mechanism for piercing a drug compartment and a propellant compartment, the piercing mechanism comprising at least one pierce tubing, the pierce tubing comprising a lumen,
   wherein the lumen comprises a constriction for improved propellant velocity resulting in improved drug mixing or drug aerosolization; and
   wherein the drug compartment contains a drug, the propellant compartment contains a propellant, and piercing the drug compartment and the propellant compartment causes the propellant to flow into the drug compartment and aerosolize the drug for respiratory delivery through the body.

2. The system of claim 1, further comprising a spacer for holding the aerosolized drug prior to respiratory delivery.

3. A respiratory drug delivery system, comprising:
a body;
a piercing mechanism, for piercing a drug compartment and a propellant compartment;
wherein the drug compartment comprises a first and a second drug sub-compartment, the first drug sub-compartment containing a first drug, the second sub-compartment containing a second drug, and wherein the propellant compartment comprises a first and a second propellant sub-compartment, the first propellant sub-compartment containing a first propellant, the second propellant sub-compartment containing a second propellant, and wherein the piercing mechanism comprises a first and a second pierce tubing, the first pierce tubing for piercing the first drug sub-compartment and the first propellant sub-compartment for aerosolizing the first drug, the second pierce tubing for piercing the second drug sub-compartment and the second propellant sub-compartment for aerosolizing the second drug.

4. The system of claim 3, the first pierce tubing having shorter length than the second pierce tubing for staggered piercing of the drug sub-compartments and the propellant sub-compartments, resulting in staggered respiratory delivery of the first drug and the second drug.

5. A cartridge apparatus, comprising:
a first drug compartment containing a first drug;
a second drug compartment containing a second drug;
a first propellant compartment containing a first propellant for aerosolizing the first drug,
a second propellant compartment containing a second propellant for aerosolizing the second drug, wherein the first drug compartment is joined to the first propellant compartment by a common membrane, the second drug compartment is joined to the second propellant compartment by a common membrane and the first drug and propellant compartments are fastened to the second drug and propellant compartments.

6. A cartridge apparatus, comprising:
a drug compartment containing a single dose of a drug; and
a propellant compartment containing a propellant in a quantity suitable for aerosolizing the single dose of the drug,
a propellant compartment containing a propellant for aerosolizing the drug; and
a chaser compartment containing a chaser for providing secondary flow resulting in improved deposition of the drug, wherein the drug compartment is joined to the propellant compartment by a common membrane, and the propellant compartment is joined to the chaser compartment by a common membrane.

7. A method for respiratory drug delivery, comprising:
providing a cartridge according to claim 6,
releasing the propellant from the propellant compartment;
aerosolizing the drug using the released propellant;
wherein the releasing step comprises piercing the propellant compartment; and
releasing a chaser from a chaser compartment for providing a secondary flow resulting in improved deposition of the drug.

8. A method for respiratory drug delivery, comprising:
providing a cartridge comprising
a drug compartment containing a single dose of a drug; and
a propellant compartment containing a propellant in a quantity suitable for aerosolizing the single dose of the drug, wherein the drug compartment and propellant compartment are joined by a common membrane;
releasing the propellant from the propellant compartment; and
aerosolizing the drug using the released propellant;
wherein the releasing step comprises piercing the propellant compartment.

9. A cartridge comprising:
a drug compartment containing a single dose of a drug;
a propellant compartment containing a propellant in a quantity suitable for aerosolizing the single dose of the drug, wherein the drug compartment and propellant compartment are joined by a common membrane; and
a plunger mechanism comprising a pierce head, the plunger mechanism being inside the propellant compartment;
wherein movement of the plunger mechanism pierces the drug compartment and thrusts the propellant into the drug compartment, causing the propellant to aerosolize the drug for respiratory delivery.

10. A cartridge comprising:
a drug compartment containing a single dose of a drug;
a propellant compartment containing a propellant in a quantity suitable for aerosolizing the single dose of the drug, wherein the drug compartment and propellant compartment are joined by a common membrane; and
a plunger mechanism comprising a pierce head, the plunger mechanism being inside the propellant compartment;
wherein movement of the plunger mechanism pressurizes the propellant, pierces the drug compartment and thrusts the propellant into the drug compartment, causing the propellant to aerosolize the drug for respiratory delivery.

* * * * *